(12) United States Patent
Kalergis Parra et al.

(10) Patent No.: US 9,273,122 B2
(45) Date of Patent: Mar. 1, 2016

US009273122B2

(54) MONOCLONAL ANTIBODIES SPECIFIC FOR THE M2-1 ANTIGEN OF RESPIRATORY SYNCYTIAL VIRUS (RSV)

(71) Applicant: PONTIFICIA UNIVERSIDAD CATOLICA DE CHILE, Santiago (CL)

(72) Inventors: Alexis Mikes Kalergis Parra, Santiago (CL); Susan Marcela Bueno Ramirez, Santiago (CL); Jorge Eugenio Mora Alarcon, Santiago (CL); Roberto Sebastian Gomez Johnson, Santiago (CL)

(73) Assignee: Pontificia Universidad Catolica de Chile (CL)

( * ) Notice: Subject to any disclaimer, the term of this patent is extended or adjusted under 35 U.S.C. 154(b) by 0 days.

(21) Appl. No.: 14/360,219

(22) PCT Filed: Nov. 23, 2012

(86) PCT No.: PCT/IB2012/056688
§ 371 (c)(1),
(2) Date: Aug. 8, 2014

(87) PCT Pub. No.: WO2013/076702
PCT Pub. Date: May 30, 2013

(65) Prior Publication Data
US 2014/0348858 A1    Nov. 27, 2014

(30) Foreign Application Priority Data

Nov. 25, 2011    (CL) .................................. 3002-2011

(51) Int. Cl.
*C07K 16/10*    (2006.01)
*G01N 33/569*   (2006.01)

(52) U.S. Cl.
CPC ...... *C07K 16/1027* (2013.01); *G01N 33/56983* (2013.01); *C07K 2317/20* (2013.01); *C07K 2317/56* (2013.01); *G01N 2333/135* (2013.01)

(58) Field of Classification Search
None
See application file for complete search history.

(56) References Cited

U.S. PATENT DOCUMENTS

| 5,762,905 | A | 6/1998 | Burton et al. | |
|---|---|---|---|---|
| 6,790,611 | B2 | 9/2004 | Lassen et al. | |
| 2002/0068066 | A1* | 6/2002 | Shi et al. | 424/185.1 |

FOREIGN PATENT DOCUMENTS

| CL | 0094896 | 2/1999 |
|---|---|---|
| CN | 101130765 | 2/2008 |
| WO | WO 95/04081 | 2/1995 |
| WO | WO 02/102975 | 12/2002 |
| WO | WO 2009/088159 | 7/2009 |

OTHER PUBLICATIONS

Gomez et al., J Med Virology 2014 vol. 86, pp. 1256-1266.*
Erdman et al. "Monoclonal antibody-based capture enzyme immunoassays for specific serum immunoglobulin G (IgG), IgA, and IgM antibodies to respiratory syncytial virus." *J. Clin. Microbiol.* 28(12):2744-2749 (1990).
Li et al. "Association of Respiratory Syncytial Virus M Protein with Viral Nucleocapsids Is Mediated by the M2-1 Protein." *J. of Virology.* 82(17):8863-8870 (2008).
Murray et al. "Characterization of Monoclonal Antibodies Raised against Recombinant Respiratory Syncytial virus Nucleocapsid (N) Protein: Identification of a Region in the Carboxy Terminus of N Involved in the Interaction with P Protein." *Virology.* 289:252-261 (2001).
Reichert. "Antibody-based therapeutics to watch in 2011." *Landes Bioscience. mAbs.* 3(1):76-99 (2011).
Van Den Hoogen et al. "Antigenic and Genetic Variability of Human Metapneumoviruses." *Emerging Infectious Diseases.* 10(4):658-666 (2004).
Initiative for Vaccine Research (IVR) Acute Respiratory Infections (Update Sep. 2009) http://apps.who.int/vaccine_research/diseases/ari/en/index2.html retrieved Jun. 2, 2014.
International Search Report for PCT/IB2012/056688 mailed May 24, 2013 (11 pages).
Avendano et al., "Surveillance for Respiratory Syncytial Virus in Infants Hospitalized for Acute Lower Respiratory Infection in Chile (1989 to 2000)," *J. Clin. Microbiol.,* 41(10):4879-4882 (2003).

(Continued)

*Primary Examiner* — Shanon A Foley
*Assistant Examiner* — Myron Hill
(74) *Attorney, Agent, or Firm* — Merchant & Gould P.C.

(57) ABSTRACT

The use of monoclonal antibodies specific for respiratory syncytial virus (RSV). Specifically, to a monoclonal antibody IgG2A secreted by the cell line of 8A4/G9 hybridoma specifically directed to the M2-1 viral antigen, which is associated with the nucleocapside of the virus. The antibodies can be used for assays for the detection and/or determination of RSV infection. The antibodies are in the pure state and do not contain any other contaminating biological material. A method for preventing and treating the infection caused by respiratory syncytial virus (RSV) in a given host is provided, including the administration of a composition containing the monoclonal antibodies secreted by the 8A4/G9 hybridoma in sufficient doses to prevent the disease. The antibody can be humanized in order to minimize the possibility of an immune response against the same in the patient. In addition, it can be used to obtain any pharmaceutical form of the formulation of the monoclonal antibodies secreted by the 8A4/G9 hybridoma, which are suitable for the treatment or prevention of the disease caused by RSV. It also provides methods for detection and diagnosis of RSV viral antigens in biological samples using the monoclonal antibodies produced and secreted by cells of the 8A4/G9 hybridoma.

11 Claims, 9 Drawing Sheets

(56) References Cited

OTHER PUBLICATIONS

Bont et al., "Natural Reinfection with Respiratory Syncytial Virus does not Boost Virus-Specific T-Cell Immunity." *Pediatric Research.*, 52(3):363-367 (2002).

Bourgeois et al. "Use of synthetic peptides to locate neutralizing antigenic domains on the fusion protein of respiratory syncytial virus." *J. of Gen. Virology.* 72:1051-1058 (1991).

Bryce et al. "Who estimates the causes of death in children." *Lancet.* 365:1147-1152 (2005).

Cabalka. "Physiologic risk factors for respiratory viral infections and immunoprophylaxis for respiratory syncytial virus in young children with congenital heart disease." *Pediatr. Infect. Dis. J.* 23(1):S41-50 (2004).

Chomcynski. "A reagent for the single-step simultaneous isolation of RNA, DNA and proteins from cell and tissue samples." *Biotechniques.* 15(3):532-534, 536-537 (1993).

\* cited by examiner

IgG VH-8A4/G9:
ATGAAGTTGGGGTTCAGCTGGATTTTCCTTGTCCTTGTTTTAAAAGGT
GTCCAGTGTGAAATAATTCTGGTGGAGTCTGGGGGAGGCTTAGTGAG
GCCTGGAGGGTCCCTGAAACTCTCCTGTGCAGCCTCTGGATTCACTT
TCAGTCACTATGCCATGTCTTGGGCTCGCCAGACTCCGGAGAAGAG
GCTGGAGTGGGTCGCAACCATTAATAGTGGTGGTAGTTATACCTACTA
TCCAGACAGTGTGAAGGGGCGATTCACCATCTCCAGAGACAATGCC
AAGAATTCCCTATACCTGCAAATGAGCAGTCTGAGGTCTGAGGACAC
GGCCATGTATTACTGTGCAAGAAAGGGGGCTATGGACTACTGGGGTC
AAGGAACCTCAGTCACCGTCTCTTCAGCCAAAACAACAGCCCCA

IgGκ VL-8A4/G9:
ATGGAGACAGACACACTCCTGCTATGGGTACTGCTGCTCTGGGTTCC
AGGTTCCACTGGTGACATTGTGCTGACACAGTCTCCTGCTTCCTTAG
CTGTATCTCTGGGGCAGAGGGCCACCATCTCATACAGGGCCAGCAA
AAGTGTCAGTACATCTGGCTATAGTTATATGCACTGGAACCAACAGAA
ACCAGGACAGCCACCCAGACTCCTCATCTATCTTGTATCCAACCTAG
AATCTGGGGTCCCTGCCAGGTTCAGTGGCAGTGGGTCTGGGACAGA
CTTCACCCTCAACATCCATCCTGTGGAGGAGGAGGATGCTGCAACCT
ATTACTGTCAGCACATTAGGGAGCTTACACGTTCGGAGGGGGGACC
AAGCTGGAAA

B

IgG VH-8A4/G9:
MKLGFSWIFLVLVLKGVQCEIILVESGGGLVRPGGSLKLSCAASGFTFSH
YAMSWARQTPEKRLEWVATINSGGSYTYYPDSVKGRFTISRDNAKNSL
YLQMSSLRSEDTAMYYCARKGAMDYWGQGTSVTVSSAKTTAP

IgGκ VL-8A4/G9:
METDTLLLWVLLLWVPGSTGDIVLTQSPASLAVSLGQRATISYRASKSVS
TSGYSYMHWNQQKPGQPPRLLIYLVSNLESGVPARFSGSGSGTDFTLN
IHPVEEEDAATYYCQHIRELTRSEGGPSWK*NGLMLHQLY

FIGURE 4
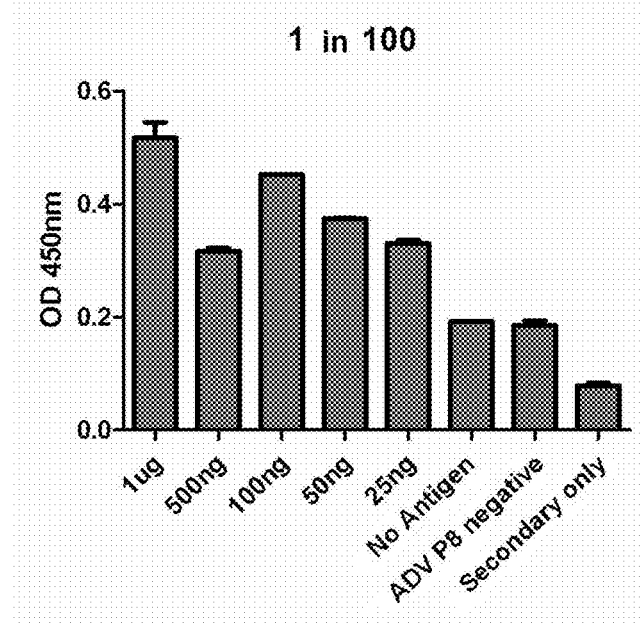
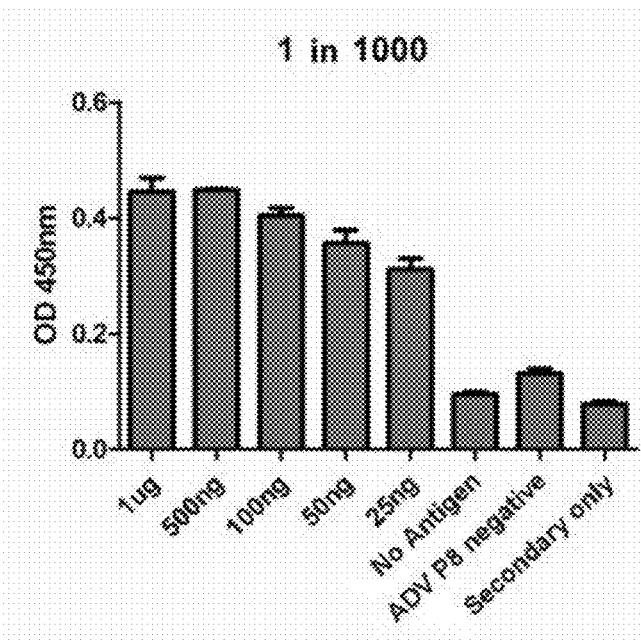

FIGURE 5
A
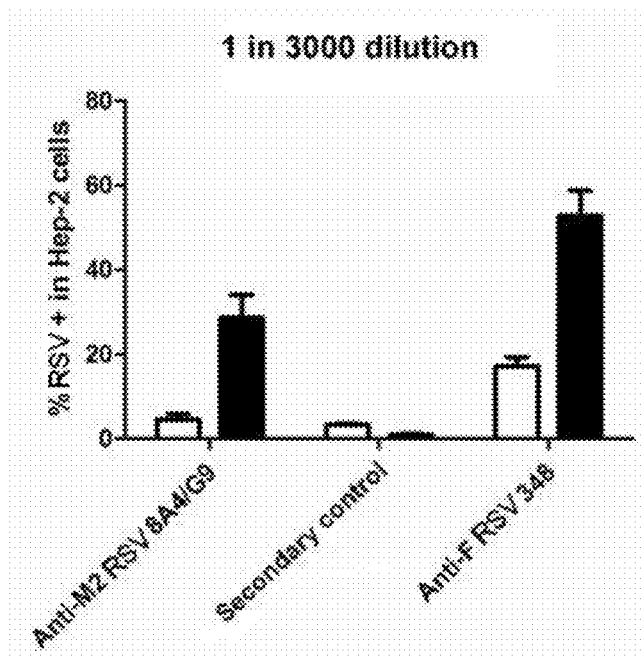
B
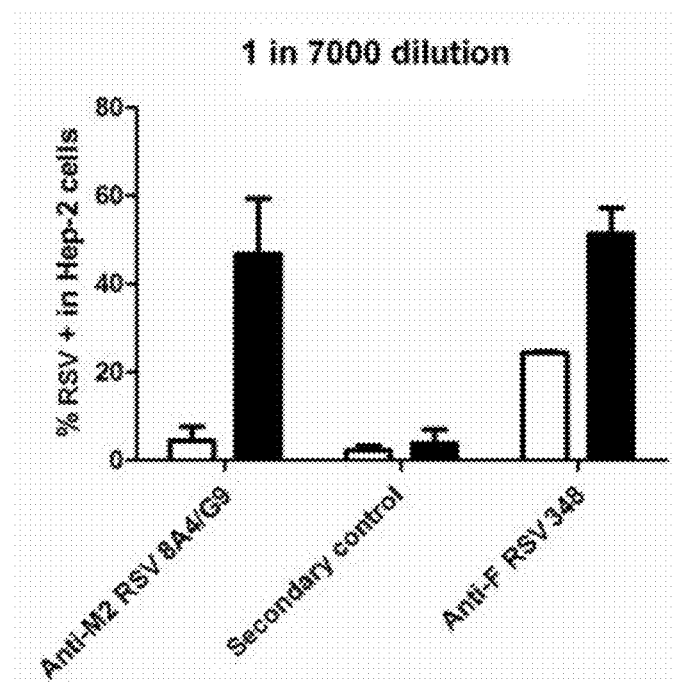

FIGURE 6
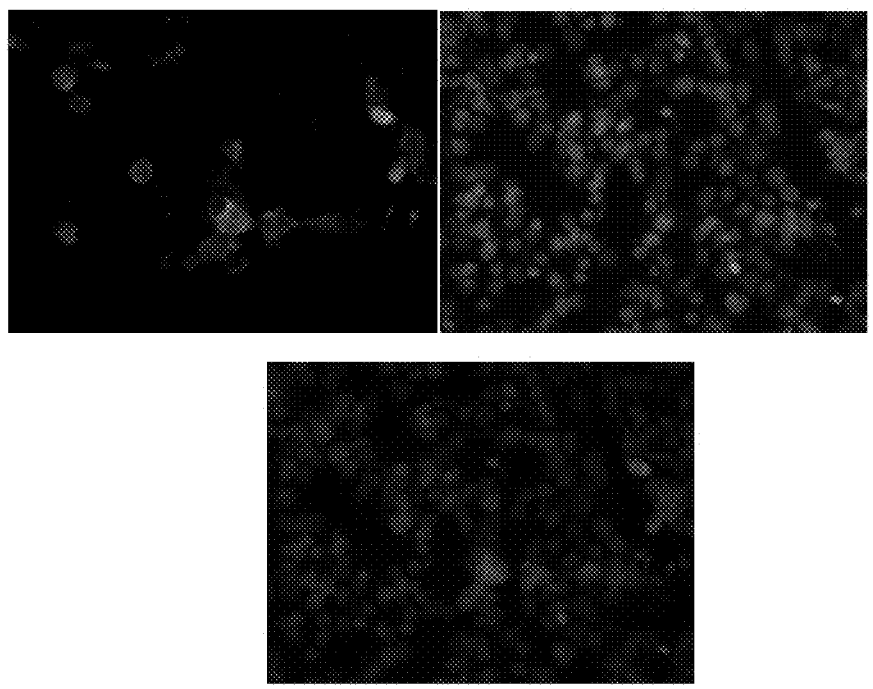
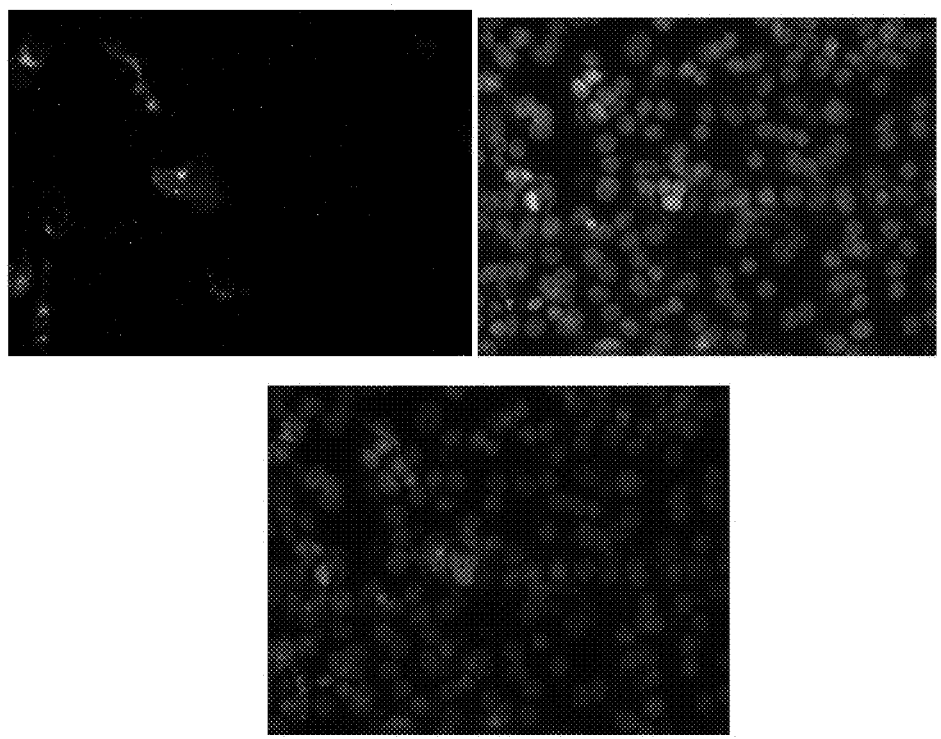

FIGURE 7
A
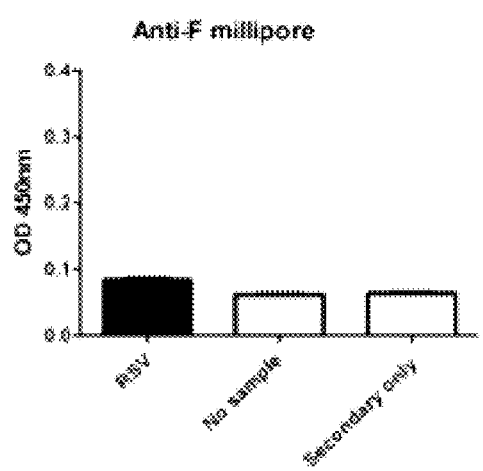
B
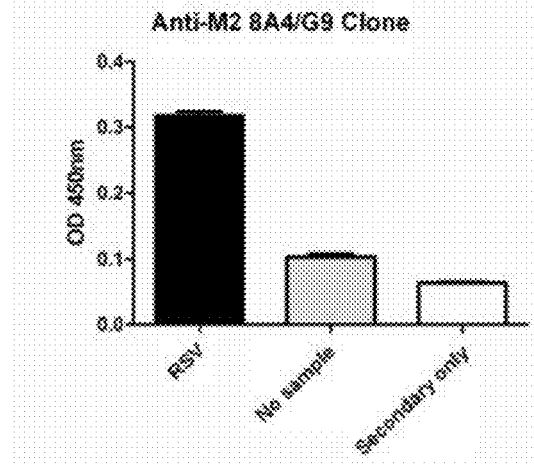
C
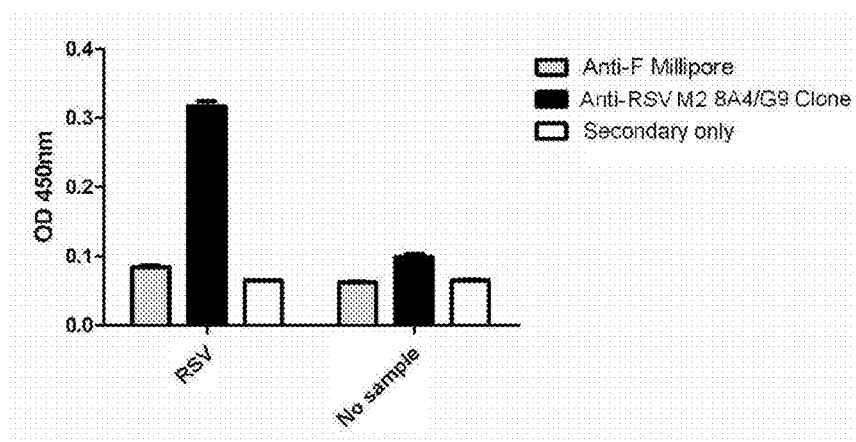

SEQUENCE LISTING

<160> NUMBER OF SEQ ID NOS: 8

<210> SEQ ID NO 1
<211> LENGTH: 420
<212> TYPE: DNA
<213> ORGANISM: Mus musculus
<220> FEATURE:
<221> NAME/KEY: misc_feature
<222> LOCATION: (1)..(420)
<223> OTHER INFORMATION: hybridoma 8A4/G9 - IgG VH

<400> SEQUENCE: 1

```
atgaagttgg ggttcagctg gattttcctt gtccttgttt taaaaggtgt ccagtgtgaa    60
ataattctgg tggagtctgg gggaggctta gtgaggcctg gagggtccct gaaactctcc   120
tgtgcagcct ctggattcac tttcagtcac tatgccatgt cttgggctcg ccagactccg   180
gagaagaggc tggagtgggt cgcaaccatt aatagtggtg gtagttatac ctactatcca   240
gacagtgtga aggggcgatt caccatctcc agagacaatg ccaagaattc cctatacctg   300
caaatgagca gtctgaggtc tgaggacacg gccatgtatt actgtgcaag aaaggggct   360 atggactact gggtcaagg aacctcagtc accgtctctt cagccaaaac aacagcccca   420
```

<210> SEQ ID NO 2
<211> LENGTH: 384
<212> TYPE: DNA
<213> ORGANISM: Mus musculus
<220> FEATURE:
<221> NAME/KEY: misc_feature
<222> LOCATION: (1)..(384)
<223> OTHER INFORMATION: hybridoma 8A4/G9 - IgGk VL

<400> SEQUENCE: 2

```
atggagacag acacactcct gctatgggta ctgctgctct gggttccagg ttccactggt    60
gacattgtgc tgacacagtc tcctgcttcc ttagctgtat ctctgggca gagggccacc   120 atctcataca gggccagcaa agtgtcagt acatctggct atagttatat gcactggaac   180
caacagaaac aggacagcc acccagactc ctcatctatc ttgtatccaa cctagaatct   240
ggggtccctg ccaggttcag tggcagtggg tctgggacag acttcaccct caacatccat   300
cctgtggagg aggaggatgc tgcaacctat tactgtcagc acattaggga gcttacacgt   360
tcggaggggg gaccaagctg gaaa                                          384
```

<210> SEQ ID NO 3
<211> LENGTH: 140
<212> TYPE: PRT
<213> ORGANISM: Mus musculus
<220> FEATURE:
<221> NAME/KEY: MISC_FEATURE
<222> LOCATION: (1)..(140)
<223> OTHER INFORMATION: hybridoma 8A4/G9 - IgG VH

<400> SEQUENCE: 3

```
Met Lys Leu Gly Phe Ser Trp Ile Phe Leu Val Leu Val Leu Lys Gly
1               5                   10                  15

Val Gln Cys Glu Ile Ile Leu Val Glu Ser Gly Gly Gly Leu Val Arg
            20                  25                  30

Pro Gly Gly Ser Leu Lys Leu Ser Cys Ala Ala Ser Gly Phe Thr Phe
        35                  40                  45

Ser His Tyr Ala Met Ser Trp Ala Arg Gln Thr Pro Glu Lys Arg Leu
    50                  55                  60
```

Glu Trp Val Ala Thr Ile Asn Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Ser Ser Leu Arg Ser Glu Asp Thr Ala Met
            100                 105                 110

Tyr Tyr Cys Ala Arg Lys Gly Ala Met Asp Tyr Trp Gly Gln Gly Thr
        115                 120                 125

Ser Val Thr Val Ser Ser Ala Lys Thr Thr Ala Pro
    130                 135                 140

<210> SEQ ID NO 4
<211> LENGTH: 128
<212> TYPE: PRT
<213> ORGANISM: Mus musculus
<220> FEATURE:
<221> NAME/KEY: MISC_FEATURE
<222> LOCATION: (1)..(128)
<223> OTHER INFORMATION: hybridoma 8A4/G9 - IgGk VL

<400> SEQUENCE: 4

Met Glu Thr Asp Thr Leu Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Pro Ser Trp Lys
        115                 120                 125

<210> SEQ ID NO 5
<211> LENGTH: 33
<212> TYPE: DNA
<213> ORGANISM: Artificial Sequence
<220> FEATURE:
<223> OTHER INFORMATION: heavy chain MuIgVH5'-A primer

<400> SEQUENCE: 5
gggaattcat grasttskgg ytmarctkgr ttt                                33

<210> SEQ ID NO 6
<211> LENGTH: 35
<212> TYPE: DNA
<213> ORGANISM: Artificial Sequence
<220> FEATURE:
<223> OTHER INFORMATION: heavy chain MuIgVH5'-F primer

<400> SEQUENCE: 6
actagtcgac atgaacttyg ggytsagmtt grttt                              35

<210> SEQ ID NO 7
<211> LENGTH: 33
<212> TYPE: DNA

```
<213> ORGANISM: Artificial Sequence
<220> FEATURE:
<223> OTHER INFORMATION: light chain MulgkVL5'-B primer

<400> SEQUENCE: 7
gggaattcat ggagacagac acactcctgc tat                              33

<210> SEQ ID NO 8
<211> LENGTH: 39
<212> TYPE: DNA
<213> ORGANISM: Artificial Sequence
<220> FEATURE:
<223> OTHER INFORMATION: light chain MulgkVL5'-C primer

<400> SEQUENCE: 8
actagtcgac atggagwcag acacactsct gytatgggt                        39
```

MONOCLONAL ANTIBODIES SPECIFIC FOR THE M2-1 ANTIGEN OF RESPIRATORY SYNCYTIAL VIRUS (RSV)

This application is a National Stage Application of PCT/IB2012/056688, filed 23 Nov. 2012, which claims benefit of Serial No. 3002-2011, filed 25 Nov. 2011 in Chile and which applications are incorporated herein by reference. To the extent appropriate, a claim of priority is made to each of the above disclosed applications.

FIELD OF INVENTION

The present invention relates to monoclonal antibodies that recognize the M2-1 protein of human respiratory syncytial virus (RSV), useful for development of diagnostic methods for RSV infection and production of pharmaceutical compositions for the treatment and/or prophylaxis of RSV infection.

BACKGROUND OF THE INVENTION

Acute respiratory tract infections are the major cause of pediatric hospitalizations and deaths worldwide (Bryce, Boschi-Pinto et al. 2005). During the cold months, respiratory tract infections caused by viruses are exacerbated and produce an increased number of cases, a situation that acquires the features of an outbreak. The viruses causing these epidemics in the pediatric population are mainly respiratory syncytial virus (RSV), adenovirus (ADV) and influenza virus. Another causative agent of respiratory tract infections is metapneumovirus (hMPV), a recently identified virus and which causes severe respiratory infections in children under two years of age (van den Hoogen, Herfst et al. 2004), although its diagnosis is not widespread. However, RSV is the major causative agent of acute respiratory tract infections in infants worldwide, causing severe outbreaks in winter months. According to WHO, the virus infects 64 million people annually, of which 160,000 die (www.who.int). Infection by this virus causes a wide range of clinical conditions, which may be mild such as rhinitis or more severe, such as pneumonias or bronchiolitis; the most severe diseases are seen in infants, preterm, children with congenital heart diseases and in immunocompromised children (Cabalka 2004). In addition, the infection caused by this virus is extremely common and recurrent, since almost 100% of children over three years have presented at least one episode of RSV infection (Bont, Versteegh et al. 2002). Since this infection does not leave adequate immunological memory reinfections are frequent, declining its severity with increasing patient age. However, reinfected individuals act as reservoirs and are a source of infection for infants younger than 1 year of age, those who develop severe respiratory symptoms. In Chile, during the cold months (May-August) this virus is the cause of 70% of acute lower respiratory tract infections requiring hospitalization (Avendano, Palomino et al. 2003), being the cause of the death of 0.1% of them. Although this percentage is low, the large number of cases makes the number of deaths very significant. This situation causes the saturation of emergency healthcare services, which often has made necessary the implementation of emergency measures in health services, including the conversion of hospital beds for pediatric patients, suspension of elective and scheduled surgeries and recruitment of supporting staff during the months when the outbreak occurs. The RSV diagnostic method often used in hospital facilities is a diagnostic test based on the detection of viral antigens by direct immunofluorescence of nasopharyngeal swabs. The limitation of this test is related to the need of having trained personnel for processing and analysis of samples and, besides, the results of said test are not immediately acquire, leaving a period of time within which the patient remains undiagnosed, but the infection continues its course. Due to this problem, the development of efficient monoclonal antibodies, which can be used for creating alternative detection test for RSV requiring minimum training and being fast to perform (as, e.g., immunochromatographic test), appear as necessary alternative to meet this need, since they allow the specific recognition of viral antigens in samples from patients infected with RSV, and also requiring a small amount of sample. Thus, our invention results in an antibody capable to detect low amounts of RSV antigens very efficiently and effectively, allowing the development of a fast, efficient and accurate alternative detection and diagnostic method for patients infected with RSV, in order to establish an appropriate and early treatment having effect in the development of the disease. Furthermore, the efficiency of our antibody allows us to suggest their use for the preparation of pharmaceutical compositions for treatment and/or prophylaxis of RSV infection. The antibody of the invention is specifically a monoclonal antibody recognizing M2-1 protein of human RSV and which is secreted by 8A4/G9 hybridoma.

SUMMARY OF THE INVENTION

The present invention relates to the use of monoclonal antibodies specific for respiratory syncytial virus (RSV). Specifically, the invention relates to a monoclonal antibody IgG2A secreted by the cell line of 8A4/G9 hybridoma specifically directed to the M2-1 viral antigen, which is associated with the nucleocapside of the virus. The antibodies can be used for assays for the detection and/or determination of RSV infection. Said antibodies are in the pure state and do not contain any other contaminating biological material. In the description of the antibody of the invention are used indistinctly the terms M2-1 protein and M2 protein.

In another aspect of the invention a method for preventing and treating the infection caused by respiratory syncytial virus (RSV) in a given host is provided, comprising the administration of a composition containing the monoclonal antibodies secreted by the 8A4/G9 hybridoma in sufficient doses to prevent the disease. The antibody can be humanized in order to minimize the possibility of an immune response against the same in the patient.

In addition, the invention can be used to obtain any pharmaceutical form of the formulation of the monoclonal antibodies secreted by the 8A4/G9 hybridoma, which are suitable for the treatment or prevention of the disease caused by RSV.

The invention also provides methods for detection and diagnosis of RSV viral antigens in biological samples using the monoclonal antibodies produced and secreted by cells of the 8A4/G9 hybridoma by assays such as ELISA, immunofluorescence microscopy, immunohistochemistry, flow cytometry, cell purification (CellSorter, by fluorescence, by association to magnetic beads or any other separation method using the antibody), immunoprecipitation, Western blot and chromatography. Samples may be in vitro cells infected with RSV or samples obtained from individuals suspected of RSV infection. In the case of a person samples, they may be nasal secretions, nasal irrigations, pharyngeal secretions, bronchial secretions or washings or any other appropriate type of sample. The invention provides the opportunity to develop a method for isolation and detection of respiratory syncytial virus in biological samples and cell cultures by contacting them with the monoclonal antibodies produced and/or secreted by the cell lines of 8A4/G9 hybridoma coupled to any type of solid support, as, e.g., nitrocellulose, nylon membrane or another support. The invention provides the opportunity for developing kits for rapid detection of Respiratory Syncytial Virus or the like, containing antibodies produced by 8A4/G9 hybridoma. It also provides the possibility of incorporating any kind of molecule or substrate chemically bound to the monoclonal antibodies secreted by the 8A4/G9 hybridoma, such as fluorophores, biotin, radioisotopes, metals, enzymes and/or any chemical element coupled to the monoclonal antibodies secreted by the 8A4/G9 hybridoma, as screening, treatment, analysis and/or diagnostic method in biological samples.

DESCRIPTION OF THE DRAWINGS

FIG. 1: Nucleotide sequences and amino acid sequences deduced from the variable regions of the light and heavy chains of immunoglobulin G secreted by the 8A4/G9 hybridoma A. Nucleotide sequence of the messenger RNA encoding the heavy chain (IgGVH-8A4/G9 (SEQ ID NO: 1), upper panel) and light chain (IgκV$_L$-8A4/G9 (SEQ ID NO: 2), lower panel), obtained by sequencing the complementary DNA prepared from a sample of total RNA purified from the actively growing hybridoma B. Deduce amino acid sequence for the variable region of the heavy chain (IgGVH-8A4/G9 (SEQ ID NO: 3), upper panel) and light chain (IgκV$_L$-8A4/G9 (SEQ ID NO: 4), lower panel).

FIG. 4: Graphs showing the sensitivity results of monoclonal anti-M2 antibody at 1 in 100 dilution (4.25 ug/ml) (FIG. 4A) and at 1 in 1,000 dilution (425 ng/ml) (FIG. 4B). Each graph shows the antibody ability to detect the antigen in different amounts. The amounts of antigen tested were 1 ug (first bar), 500 ng (second bar), 100 ng (third bar), 50 ng (fourth bar), 25 ng (fifth bar), control with no antigen (sixth bar), specificity control in which adenovirus P8 protein is used as antigen (seventh bar) and a secondary anti-mouse IgG-HRP antibody (eighth bar).

FIG. 5: Graphs showing data detection of RSV infected HEp-2 cells with monoclonal anti-M2 antibody (425 μg/ml), at a dilution of 1 in 3,000 (141.6 ng/ml) (FIG. 5A) and at a dilution of 1 in 7,500 (56.6 ng/ml) (FIG. 5B) by flow cytometry. Each graph shows the antigen detection in infected cells (black bars) and uninfected cells (open bars), using the monoclonal anti-M2 antibody (first pair of bars), a control with only the secondary anti-mouse IgG-FITC antibody (second pair of bars) and a positive control with an anti-RSV F antibody (Bourgeois, Corvaisier et al. 1991) ((third pair of bars). This latter antibody was used at a dilution of 1 in 1,000 in both assays.

FIG. 6: FIG. 6A shows immunofluorescence images of HEp-2 cells infected and stained with monoclonal anti-M2 antibody of the invention. FIG. 6B shows the immunofluorescence images of HEp-2 cells infected and stained with monoclonal anti-F antibody from Millipore. In the images, the upper left shows an image of the staining only in the green channel, corresponding to the label for RSV M2, the upper right image shows staining only in the blue channel corresponding to the nuclear label and the bottom image shows the two channels together.

FIG. 7: Graphs showing the results of determination of RSV by ELISA assay for commercial anti-F antibody (FIG. 7A) and for the monoclonal anti-M2-1 antibody (FIG. 7B). Each graph shows the ability of the antibody to detect the antigen (first bar), a control with no antigen (second bar) and a control in which only a secondary antibody is used (third band). FIG. 7C corresponds to a graph showing the results of both antibodies. They show that the monoclonal anti-M2-1 antibody is able to better detect virus particles than the commercial anti-F antibody.

In FIGS. 9A to 9E, the first bar of the graphs represents the viral antigen detection using the detection antibody (polyclonal antibody) at a dilution of 1 in 1,000; the second bar represents the viral antigen detection using the detection antibody at a dilution of 1 in 2,000; the third bar corresponds to a control in which has not been used detection antibody; and the fourth and fifth bar shows the result of the assay performed without activation of the plate with monoclonal antibody, but using detection antibody in dilutions of 1 in 1,000 and 1 in 2,000, respectively. FIG. 9F shows a graph corresponding to controls, where the first two bars show the result of the test with no sample, at two dilutions of the detection antibody (1 in 1,000 and 1 in 2,000), and the third and fourth bar shows the result of the assay with no sample and with no capture antibody and with two dilutions of the detection antibody (1 in 1,000 and 1 in 2,000).

DETAILED DESCRIPTION OF THE INVENTION

Figure 2:
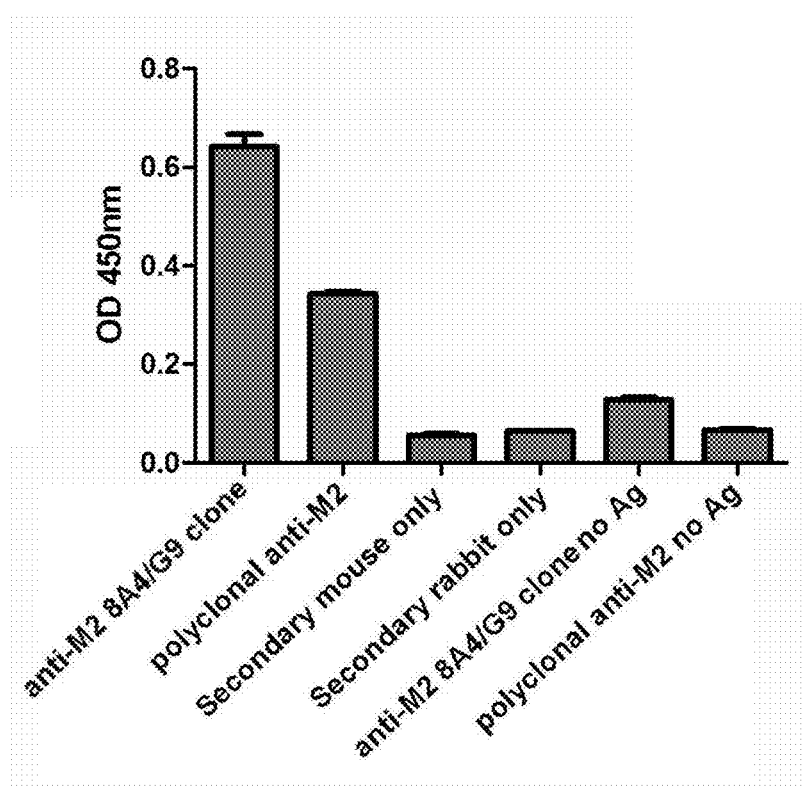
FIG. 2: Graph showing detection test results for the M2 antigen of RSV by ELISA, using the anti-M2 antibody of 8A4/G9 clone (first bar), polyclonal anti-M2 antibodies produced in rabbit (second bar), secondary anti-mouse IgG-HRP antibody only (third bar), the secondary anti-rabbit IgG-HRP antibody (fourth bar), anti-M2 antibody of 8A4/G9 clone but with no presence of antigen (fifth bar) and polyclonal anti-M2 antibodies produced in rabbit but with no presence of antigen (sixth bar). It can be seen that monoclonal anti-M2 antibody from 8A4/G9 clone detects more efficiently the M2 antigen than the polyclonal antibody produced in rabbit.

The present invention relates to the ability of monoclonal IgG2a antibody for the specific recognition of an antigen derived from the M2-1 protein, which is associated with the Respiratory Syncytial Virus (RSV) nucleocapsid.

A monoclonal antibody is a type of homogeneous antibody characterized by being able of recognize specifically a single antigen. They are produced by a single hybrid cell (hybridoma), which is the product of the fusion B lymphocyte clone and tumoral plasma cell. The property of binding specifically and with high affinity to an antigen has promoted the development of monoclonal antibodies as a useful tool for detection of molecules that generate a great scientific, clinical and industrial interest. At present, monoclonal antibodies are widely used in both basic and applied research, because of their specificity and reproducibility, which allows for better substantiated research. However, it is in the area of biomedicine where monoclonal antibodies have had enormous practical applications, either for diagnosis and treatment of many infectious diseases, and as therapy for other diseases. Although monoclonal antibodies are used in all kinds of techniques for detection and diagnosis, is in the design of in vitro diagnostic kits where have been obtained the best results. For this, there are currently several rapid detection kits, such as pregnancy tests, based on the determination of human chorionic gonadotropin (hCG) levels in urine using anti-hCG antibody. Furthermore, monoclonal antibodies for therapeutic use have become really important. Currently there are therapeutic treatments for various diseases using commercial monoclonal antibodies as Alemtuzumad, Gemtuzumab ozogamicin, Rituximab, Trastumab etc. (Reichert).

RSV is an enveloped RNA virus belonging to the Paramyxoviridae family, subfamily Pneumovirinae. Its RNA is transcribed into 10 mRNA, each one of which encodes a viral protein, except for the M2 mRNA, which has two open reading frames (ORF) overlapped in 22 nucleotides encoding two different proteins: ORF-1 encoding M2-1 and ORF-2 encoding M2-2. The proteins encoded by other mRNAs are the nucleoprotein (N), phosphoprotein (P), L protein, matrix protein (M), NS1, NS2, SH, fusion protein (F) and G. N protein is associated with the genomic RNA to form the nucleocapsid, L is an RNA polymerase associated with the nucleocapsid, P interacts with N and L, M is a non-glycosylated protein that is located on the inner side of the viral envelope, NS1 and NS2 are nonstructural proteins, and SH, G and F are part of the viral envelope. RSV diagnostic kits developed until now use antibodies against F, N and/or G proteins of RSV, and the antibodies suggested for the treatment or prophylaxis of RSV infection are also directed to the same proteins (CL948-96, CN101130765, U.S. Pat. No. 6,790,611, WO2009088159, (Erdman and Anderson 1990), (Murray, Loney et al. 2001)). Currently, there are no RSV diagnostic kits or pharmaceutical compositions for treatment and/or prophylaxis of RSV infection using antibodies that bind to the RSV M2-1 protein.

M2-1 is a polypeptide with a molecular weight of 22 kD that functions as a transcriptional factor, which prevents premature termination during transcription and, thus, facilitates transcriptional reading at the junction of genes and allows access of RSV polymerase to downstream transcriptional units. This process occurs throughout the replication cycle of RSV, where the M2-1 protein, newly synthesized, is associated to the nucleocapsid through its interaction with P. In addition, it was observed that the M protein is associated to the nucleocapsid only in presence of M2-1, and has been suggested that this interaction allows to shutdown virus transcriptase activity, presumably to start the assembly and budding by interacting with the envelope glycoproteins (Li, Jans et al. 2008). In the present description the terms M2-1 protein and M2 protein are used interchangeably.

From our research related to the effects of viral antigens derived from Respiratory Syncytial Virus (RSV) on the immune system, we have generated murine monoclonal antibodies specific for detecting RSV antigens that have advantages over commercially available antigens. Specifically, the monoclonal antibody produced by 8A4/G9 hybridoma proved to be very useful for determining RSV infection by in vitro and in vivo immunological assays using various detection techniques. Because of this, these antibodies allow to have a valuable tool for detection, diagnosis and/or therapy of infection caused by Respiratory Syncytial Virus in any biological sample where is present a low viral load. This monoclonal antibody may have many therapeutic and diagnostic applications, such as use in immunoblot techniques, immunofluorescence, immunochromatography, flow cytometry, production of pharmaceutical forms that comprise the same, or any other application involving their use. The antibody can be bound to a label that allows its detection. Examples of possible labels correspond to fluorophores, biotin, radioisotopes, metals, enzymes and any other suitable label for antibodies.

The monoclonal antibody of the invention can be found in its natural form as secreted by the hybridoma, or alternatively as antigen binding fragments. The antigen binding fragments are antibody fragments able of binding to antigen, such as Fab or Fab' fragments. In the present application, the applications of the antibody of the invention, although mention the use of the antibody, also include the use of binding fragments of monoclonal anti-M2 antibody. Furthermore, in the case of the generation of compositions comprising the antibody of the invention, such compositions may comprise the murine antibody or the humanized or chimeric antibody of the invention. This is especially useful in compositions for human administration and as a way to minimize the possibility that the immune system of the individual treated with the composition could generate a response against the antibodies of the invention.

Examples demonstrating the different applications of the monoclonal antibody of the invention are described below.

EXAMPLE 1

Determination of the Nucleotide Sequence Encoding the Variable Region Light Chain (VL) and Variable Region Heavy Chain (VH) of the Anti M2-1 Immunoglobulin Secreted by the 8A4/G9 Hybridoma 8A4/G9 hybridoma was grown in DMEM-highglucose medium from GIBCO-BRL (Invitrogen, Cat. No.: SH30243.01) supplemented with 3.7 g/L sodium bicarbonate and 10% fetal bovine serum (HyClone) at 37° C. with 10% $CO_2$. When the cell density reached 700,000 cells/ml, $3.5\times10^6$ cells were recovered and from these cells a purification of total RNA was performed using Trizol (Invitrogen, Cat No.: 15596-018), as previously described (Chomczynski 1993). 0.5 μg of RNA was retrotranscribed to complementary DNA using the Impron II kit from Promega and 2 μl of the reaction were used to perform a polymerase chain reaction (PCR) using primers supplied in the Ig-Primer set Kit from Novagen (Cat No.: 69831-3) following to suppliers instructions, in a Axygen MaxyGene™ Thermal Cycler. PCR products were obtained with the primers whose sequences are: For the heavy chain MuIgVH5'-A: 5'GGGAATTCATGRASTTSKGGYTMARCTKGRTTT3' (SEQ ID NO: 5) and MuIgVH5'-F: 5'ACTAGTCGACATGAACTTYGGGYTSAGMTTGRTTT3' (SEQ ID NO: 6); for the light chain MuIgκ$V_L$5'-B: 5'GGGAATTCATGGAGACAGACACACTCCTGCTAT 3' (SEQ ID NO: 7) and MuIgκ$V_L$5'-C:

5'ACTAGTCGACATGGAGWCAGACA-
CACTSCTGYTATGGGT3' (SEQ ID NO: 8). PCR products
were cloned into the pCr TOPO-TA cloning vector (Invitrogen, Cat No.: K450001SC), following the suppliers instructions, and sequenced by the sequencing service of the Pontificia Universidad Católica de Chile in a AbIprism 3130×1 Genetic Analyser (Applied Biosystem). The DNA sequence obtained is shown in FIG. 1A and the deduced amino acid sequence is shown in FIG. 1B. The amino acid sequence was obtained using the bioinformatic software Vector NTI (Invitrogen).

EXAMPLE 2

Detection Assay for RSV Antigens, Specificity of Monoclonal M2-1 Antibody for Purified RSV Antigens The objective of this assay is to demonstrate the specificity of our antibody for RSV viral antigens. The antigen detection was carried out by direct ELISA technique, where the ELISA plate was activated with 200 ng of purified antigen for 10 hours at 4° C. After that the plate was washed once with 1×PBS/0.02% Tween, and twice with 1×PBS, and the plate was then blocked for 2 hours with 1×PBS/3% BSA at room temperature. The washes were repeated and the plate was then incubated with anti-VRS M2 antibody of 8A4/G9 clone (425 µg/ml) at a dilution of 1 in 100 in 1× BS/1% BSA for 2 hours at room temperature. Washes were repeated after the completion of the incubation time and the plate was incubated with an anti-mouse IgG antibody labeled with horseradish peroxidase enzyme (Horseradish peroxidase, HRP) at a dilution of 1 in 2,000 in 1×PBS/1% BSA for 1 hour at room temperature. Finally, washes were performed and the plate was developed with 50 µl of citrate buffer/tetramethylbenzidine (TMB) (3-3'-5-5'tetramethylbenzidine, 1 mg/ml) at 9:1 dilution and 1 ul/5 ml $H_2O_2$. The reaction was stopped by adding 2M $H_2SO_4$ and the result was read at 450 nm. Anti-VRS M2 antibody of 8A4/G9 clone was used as primary antibody for antigen detection and then anti-mouse IgG labeled with HRP was used as detection antibody (secondary antibody). Polyclonal anti-VRS M2 antibody raised in rabbit in our own laboratory was used as positive control; in this case the secondary antibody is an anti-rabbit IgG antibody labeled with HRP. Controls using secondary antibody alone and no primary antibody were performed in order to determine that the secondary antibody reaction was specific to recognize the primary antibody, and also that the signal obtained is not caused by nonspecific binding of the secondary antibody to the viral antigen. Another control for determining that the reaction of the primary antibody is specific for the antigen, involved the use of antibodies on an ELISA plate that has not been activated with the antigen. The results (FIG. 2) show that the monoclonal antibody of the invention is able to recognize 200 ng of purified antigen, the signal being stronger than even the positive control with polyclonal antibodies.

EXAMPLE 3

Figure 3:
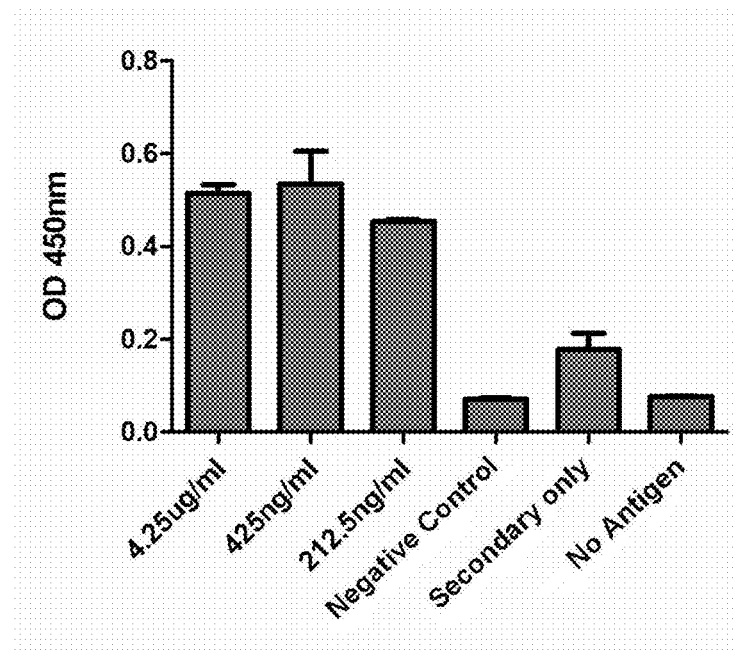
FIG. 3: Graph representing the result obtained from a performance test of the monoclonal anti-RSV M2 antibody of 8A4/G9 clone for detecting the antigen at different antibody dilutions and determining its specificity. The monoclonal anti-M2 antibody (425 μg/ml) was used at 1/100 dilution (4.25 mg/ml final concentration) (first bar), 1/1,000 dilution (425 ng/ml final concentration) (second bar), 1/2,000 dilution (212.5 ng/ml final concentration) (third bar), and also as negative control was used hMPV M2 protein as antigen (fourth bar), secondary anti-mouse IgG-HRP antibody alone (fifth bar) and control with no antigen (sixth bar).

Assay to Determine the Efficiency of the Monoclonal Antibody to Detect Viral Antigens The assay was performed to determine the maximum dilution of monoclonal anti-VRS M2 antibody of 8A4/G9 clone allowing the detection of viral antigen. For this, we used the same direct ELISA technique of Example 2, but in this case the plate was activated with 100 ng of purified antigen and anti-M2 antibody (425 µg/ml) was used at dilutions of 1 in 100, 1 in 1,000 and 1 in 2,000. The negative control was hMPV M2 protein as antigen, so as to determine that the antibody reaction is specific to RSV antigens and no for antigens of other virus. Controls using secondary antibody alone and no primary antibody were performed for determining that the reaction of the secondary antibody is specific to recognize the primary antibody, and also that the obtained signal is not caused by nonspecific binding of the secondary antibody to the viral antigen. Furthermore, in order to determine that the signal generated corresponded to the antibody-antigen specific binding, a control in which the ELISA plate was not activated with antigen prior antibodies incubation was performed. The results show (FIG. 3) that the obtained signal, despite significantly increase the antibody dilution, is kept high, and the antibody of the invention does not react nonspecifically with the hMPV M2 protein. This shows that our monoclonal anti-M2 antibody at low concentration is able to specifically detect RSV antigens.

EXAMPLE 4

Sensitivity of Monoclonal Anti-M2 Antibody to RSV Antigens

This example corresponds to an assay carry out for determining the minimum amount of antigen that our monoclonal antibody can detect. Direct ELISA assays were performed, as mentioned in the above examples. In this case, the plate is activated with purified antigen using different amounts of antigen: 1 ug, 500 ng, 100 ng, 50 ng and 25 ng. The same test was performed in two groups where two dilutions of anti-M2 antibody (425 µg/ml) were evaluated: 1 in 100 (FIG. 4A) and 1 in 1,000 (FIG. 4B). Both dilutions were chosen because they had previously shown a strong signal in the purified antigen recognition. The two assay groups include a control in which the ELISA plate is not activated with antigen (control without antigen), a negative control with Adenovirus P8 protein for determining specificity of the antibody to RSV antigen, and a control in which only secondary antibody is used. The results show that the two antibody dilutions generate a similar signal and furthermore, the antibody is capable of detecting even 25 ng of pure antigen with a quite broad signal.

EXAMPLE 5

Detection of RSV Infected Cells by Flow Cytometry, Using Anti-M2 Antibody

The objective of this assay is to demonstrate the wide range of techniques where you can use our monoclonal antibody. In the above examples, the monoclonal anti-M2 antibody was used in ELISA, and in this example the functionality of the antibody of the invention for detecting cell infection with RSV is assessed by flow cytometry. For this, HEp-2 cells infected with RSV and uninfected cells were used. Staining protocol was as follows: the cells were permeabilized with 1×PBS/0.2% Sapononin, stained with the monoclonal anti-RSV M2 antibody of 8A4/G9 clone (425 µg/ml) for 1 hour at 4° C. at two dilutions: 1 in 3,000 (FIG. 5A) and 1 in 7,500 (FIG. 5B) in 1×PBS/1% BSA, the cells were then washed with 1× PBS and centrifuged at 2,000 revolutions per minute (rpm) for 6 minutes, later they were resuspended in the same permeabilization buffer and stained with an anti-mouse IgG-FITC antibody diluted 1 in 1,000 in 1×PBS/1% BSA. Later, the cells were washed with 1×PBS and analyzed by flow cytometry. To demonstrate that the signal obtained in the flow cytometer is cause by binding of the anti-mouse IgG-FITC antibody (secondary antibody) to the antibody of the invention, a control in which only the secondary antibody was used is included. In addition, a positive control was included using an anti-RSV F protein antibody. Data obtained for both antibody dilutions were positive, as seen in FIG. 5, where we can see a marked difference between infected cells and uninfected cells, leading to the conclusion that our antibody can recognize infected cells by flow cytometry. Note that in the positive control, the antibody was used at a dilution of 1 in 1,000, which is much larger than the dilution used with the antibody of the invention. That explains why a stronger signal was obtained with the positive control than the one obtained with monoclonal anti-M2 antibody.

EXAMPLE 6

Detection of RSV Infection by Immunofluorescence Using the Monoclonal Anti-M2 Antibody This assay was performed to widen the range of techniques that allows detecting RSV infection using the disclosed invention. A fluorescence microscopy assay where HEp-2 cells infected with RSV and uninfected were stained with monoclonal anti-M2 antibody was carried out. The protocol used was as follows: the cells were fixed with 1×PBS/4% formaldehyde/0.03M sucrose for 10 minutes at 4° C., then they were washed with 1×PBS, permeabilized with 1×PBS/0.2% Saponin for 5 minutes at room temperature, monoclonal anti-M2 antibody of the invention (425 µg/ml) was added at a dilution of 1 in 200 (2.125 mg/ml) in 1×PBS/1% BSA/0.2% Saponin/0.03 M Sucrose for 10 hours at 4° C. The samples were washed with 1×PBS/0.2% Tween for five minutes and then two washes with 1×PBS were performed. The secondary anti-mouse IgG-FITC antibody is added at a dilution of 1 in 500 in 1×PBS/1% BSA for 1 hour at room temperature. Washes were repeated and the nuclei were stained with Hoescht 33258 at a concentration of 5 ug/ml for 5 minutes at room temperature, and finally they were washed with 1×PBS and they were processed for observation in a fluorescence microscope. The obtained results show (FIG. 6A) that the antibody constituent of the invention is also useful to recognize infected cells by immunofluorescence.

For comparison, the same assay described above was carried out, but with a commercial monoclonal antibody specific for the F surface antigen of RSV, widely used today (6B). Commercial antibody used is the murine antibody that detects the RSV F protein (anti-F antibody, Millipore MAB8599Clone 131-2A). In summary, HEp-2 cells infected with RSV were stained with the commercial antibody at a 1:200 dilution and then with a secondary anti-mouse IgG-FITC antibody at a dilution of 1 in 500. It was observed that the commercial antibody as able of detecting cells infected with RSV.

EXAMPLE 7

Comparative Assay Between Commercial Anti-F Antibody by Millipore and Monoclonal Anti-RSV M2 Antibody of 8A4/G9 Clone This assay corresponds to a comparative analysis between our monoclonal anti-M2-1 antibody and the commercial monoclonal antibody specific for the F surface antigen of RSV (anti-F Millipore) in ELISA. The antibody anti-F is the same used in Example 6, in which an immunofluorescence assay was performed to detect cells infected with RSV. For determining the versatility of our antibody, in this assay our anti-M2-1 antibody was compared with the anti-F antibody from Millipore in a technique other than immunofluorescence. To perform this test, the ELISA plate was activated with viral particles (RSV) for 10 hours at 4° C. Later, the plate was blocked with 1% fish gelatine for 2 hours at room temperature, and then it was washed with 1×PBS/0.02% Tween and washed twice with 1×PBS. The plate was then incubated with the two antibodies to be compared, at a dilution of 1 in 1,000 for 2 hours at room temperature. Once the time of incubation was complete, washes were again carried out and then the plate was incubated with an antibody anti-mouse IgG labeled with HRP at a dilution of 1 in 1,500. Finally, washes were repeated and the ELISA was developed with Citrate Buffer/TMB (9:1) and $H_2O_2$ (1 µl/5 ml of solution). The reaction was stopped with 50 µl of 2M $H_2SO_4$. The assay controls correspond to a negative control in which no sample was used (the plate was not previously activated with viral particles) to ensure that the signal is determined by RSV antigen recognition, and another control in which was used only secondary antibody for determining that the secondary antibody by itself does not recognize viral antigens. The results of this test are summarized in the graphs of FIG. 7. They show that at a dilution of 1 in 1000, the commercial antibody is not able to detect RSV viral particles. However, the monoclonal M2-1 antibody is capable to recognize viral particles in such dilution. That is, the antibody of the invention is effective even at dilutions where other commercial antibodies are not able to detect the antigen. Furthermore, this assay demonstrates that our antibody is effective in a variety of techniques for antigen detection.

EXAMPLE 8

Comparative Assay Between Commercial Anti-F Antibody from Millipore, Anti-RSV DHI and Monoclonal Anti-RSV M2 Antibody of 8A4/G9 Clone The antibodies compared in this ELISA assay were: monoclonal anti-M2-1 antibody of the invention, the monoclonal anti-F antibody from Millipore (Mab8599), and the monoclonal anti-RSV antibody from Diagnostic Hybrids (DHI, RSV MAbs 01-013302). The latter antibody was chosen for comparison because is widely used clinically for the diagnosis of patients positive for RSV infection and was facilitated by the centre for medical research of the Hospital Clínico de la Universidad Católica de Chile.

Figure 8:
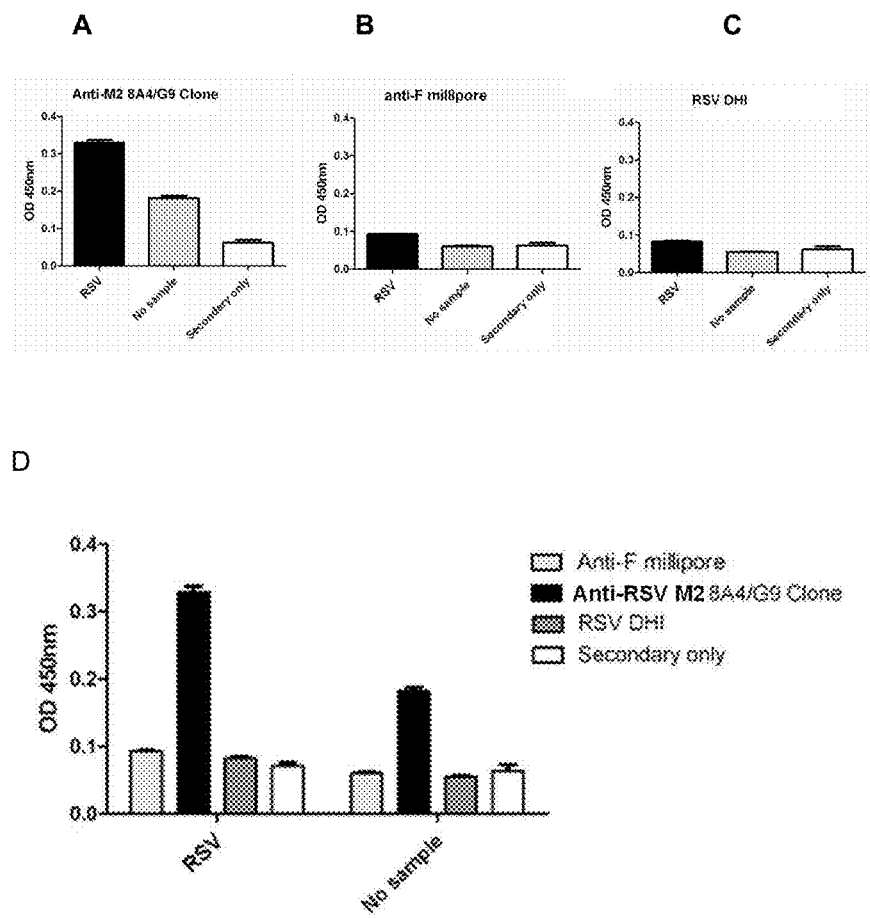
FIG. 8: Graphs representing the results of determination of RSV by ELISA assay for monoclonal anti-M2-1 antibody diluted 1 in 100 (4.25 ug/ml) (FIG. 8A), for the commercial anti-F antibody diluted 1 in 100 (10 μg/ml) (FIG. 8B) and for anti-RSV-DHI antibody diluted 1 in 10 (FIG. 8C). Each graph shows the ability of the antibody to detect the antigen (first bar), a control with no antigen (second bar) and a control in which only a secondary antibody (third band) is used. The graph of FIG. 8D shows the results of the three antibodies. It is observed that our monoclonal antibody was the only one able to recognize viral particles.

The comparative assay was carried out following the same procedure indicated in Example 7, except antibody dilutions were modified. In this case, a dilution of 1 in 100 was used for both monoclonal anti-F antibody and monoclonal anti-M2-1 antibody, and for the antibody RSV DHI a dilution 1 in 10 was used, as recommended by Diagnostic Laboratory, because a positive signal is obtained for RSV patients at that dilution. Similar to previous examples, a control with no sample, to see that the signal is determined by the recognition of RSV antigens and a control with secondary antibody only, to determine that our second antibody does not recognize viral antigens by itself, were added. The results obtained are shown in FIG. 8 and it can be seen that, at these dilutions, the commercial antibodies show no positive signal for the viral particles (FIGS. 8B and 8C), although the monoclonal M2-1 antibody was able to detect virus particles (FIG. 8A). It is worth mentioning that the use of a commercial RSV DHI antibody for diagnosis of RSV infected patients is standardized exclusively for fluorescence microscopy assays, reason that could explain no detection of RSV in ELISA. Moreover, obtaining a positive signal of monoclonal M2-1 antibody shows that this can be a valuable new tool for clinical diagnosis of RSV infected patients using the ELISA technique, currently not considered. It also opens the possibility of using this monoclonal antibody for the development of an immunodiagnostic kit.

EXAMPLE 9

Figure 9:
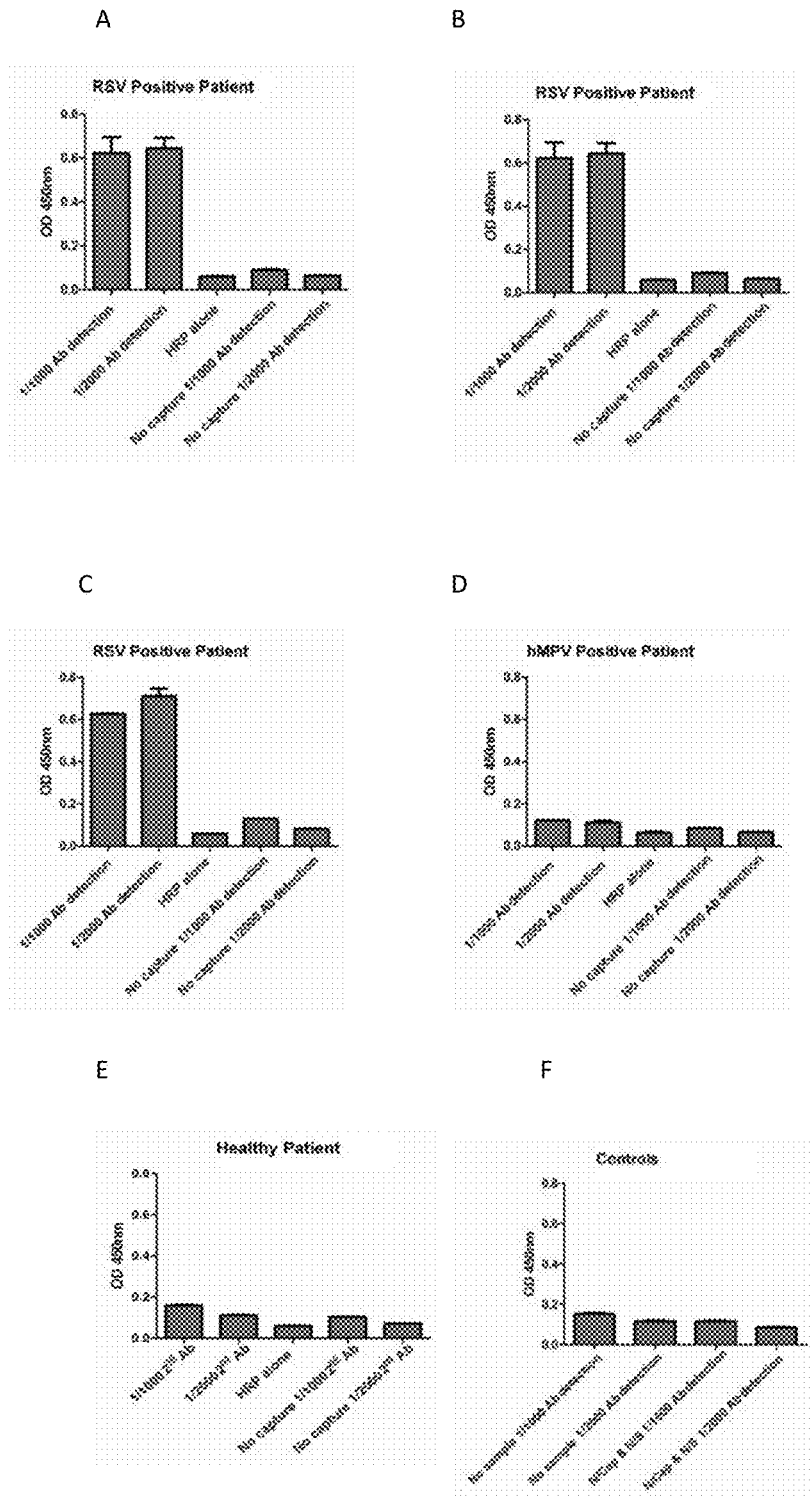
FIG. 9: Graphs showing the results obtained by sandwich ELISA using the monoclonal anti-M2 antibody of the invention, and using samples of nasopharyngeal swabs of patients previously diagnosed with or without RSV infection. Three patients positive for RSV (FIGS. 9A, 9B and 9C), one patient positive for hMPV (FIG. 9D), a healthy patient (FIG. 9E) and negative controls with no sample and with no capture antibody to determine the specifying signal (FIG. 9F) are shown.

Clinical Diagnosis of Samples of RSV Infected Patients Using Monoclonal Anti-RSV M2-1 Antibody by ELISA An ELISA assay was performed to verify the ability of the monoclonal antibody, which constitute the patent, to diagnose or detect RSV positive patients from clinical samples of nasopharyngeal swabs. Clinical samples were obtained from the Medical Research Center, Medical School, Pontificia Universidad Católica de Chile, samples that were previously diagnosed by immunofluorescence (method currently used for the diagnosis of the disease). Sandwich ELISA assays were performed on samples from patients, where the monoclonal anti-RSV M2 antibody was used to activate the plate in a dilution of 1 in 350, the plate was then blocked with 1% fish gelatin for 2 hours at room temperature. Followed by a wash performed with 1×PBS/0.02% Tween and two washes with 1×PBS, nasopharyngeal swabs samples were then incubated for 10 hours at 4° C. The samples were washed once again and incubated with a rabbit polyclonal anti-RSV M2 antibody for 2 hours at room temperature, in two dilutions: 1 in 1,000 and 1 in 2,000. Subsequently, washes were performed as described above and the samples were incubated with anti-rabbit IgG-HRP antibody (diluted 1 in 2000) and developed with citrate/TMB buffer (9:1) and 1 ul/5 ml $H_2O_2$. To stop the reaction 2M $H_2SO_4$ was added. The assay was performed on samples of three patients positive for RSV (FIGS. 9A to 9C), one hMPV positive patient (FIG. 9D), a healthy patient (FIG. 9E) and negative controls without sample and without capture antibody for determining that the signal obtained is specific (FIG. 9F). The results show that the anti-M2 antibody is able to recognize specific RSV viral antigens of nasopharyngeal swabs. Therefore, the monoclonal antibody which defines the invention may be successfully used to detect RSV viral antigens in patient samples.

The examples described herein demonstrate the specificity, efficiency, sensitivity and versatility that our RSV monoclonal anti-M2-1 antibody secreted by the cell line of 8A4/G9 hybridoma possesses. Their advantageous characteristics over other commercially available antibodies which bind to RSV, make of our antibody an effective alternative for many uses both for detection and/or identification of RSV and for the generation of pharmaceutical compositions that allows treatment and/or prophylaxis of RSV infection. The examples presented herein are a demonstration of some of the uses of monoclonal anti-RSV M2-1 antibody, but in no way limit the scope of our invention.

REFERENCES www.who.int. Initiative for Vaccine Research (IVR), Acute Respiratory Infections (Update September 2009).
CL948-96, Anticuerpos monoclonales humanos contra la proteina F del virus sincitial respiratorio (RSV), células que los producen; secuencias de ADN que los codifican; métodos para producirlos; uso de dichos anticuerpos; composición farmacéutica; método y equipo de prueba de diagnostico. BIOGEN IDEC INC., CAMBRIDGE CENTER (US).
CN101130765, Hybridomas cell strain with preserving number at CGMCC 1546, anti-respiratory syncytial virus N protein monoclone antibody and respiratory syncytial virus detecting agent box (colloidal gold method), which can detects the respiratory syncytial virus. (BEIJING ASCLE BIOENGINEERING CO., LTD). Feb. 27, 2008
U.S. Pat. No. 6,790,611, Assay for directly detecting RS virus related biological cell in a body fluid sample. BESST TEST APS. Sep. 14, 2004.
WO2009088159, Antibodies to respiratory syncytial virus. APROGEN INC. (KR). Jul. 16, 2009
Erdman D. D. & Larry J. Anderson. Monoclonal Antibody-Based Capture Enzyme Immunoassays for Specific Serum Immunoglobulin G (IgG), IgA, and IgM Antibodies to Respiratory Syncytial Virus. JOURNAL OF CLINICAL MICROBIOLOGY, December 1990, p. 2744-2749 Vol. 28, No. 12.
Murray, Jillian; Colin Loney, Lindsay B. Murphy, Susan Graham & Robert P. Yeo. Characterization of Monoclonal Antibodies Raised against Recombinant Respiratory Syncytial Virus Nucleocapsid (N) Protein: Identification of a Region in the Carboxy Terminus of N Involved in the Interaction with P Protein. Virology 2001 (289), 252±261.
Avendano, L. F., M. A. Palomino, et al. (2003). "Surveillance for respiratory syncytial virus in infants hospitalized for acute lower respiratory infection in Chile (1989 to 2000)." *J Clin Microbiol* 41(10): 4879-4882.
Bont, L., J. Versteegh, et al. (2002). "Natural reinfection with respiratory syncytial virus does not boost virus-specific T-cell immunity." *Pediatr Res* 52(3): 363-367.
Bourgeois, C., C. Corvaisier, et al. (1991). "Use of synthetic peptides to locate neutralizing antigenic domains on the fusion protein of respiratory syncytial virus." *J Gen Virol* 72 (Pt 5): 1051-1058.
Bryce, J., C. Boschi-Pinto, et al. (2005). "WHO estimates of the causes of death in children." *Lancet* 365(9465): 1147-1152.
Cabalka, A. K. (2004). "Physiologic risk factors for respiratory viral infections and immunoprophylaxis for respiratory syncytial virus in young children with congenital heart disease." *Pediatr Infect Dis J* 23(1 Suppl): S41-45.
Chomczynski, P. (1993). "A reagent for the single-step simultaneous isolation of RNA, DNA and proteins from cell and tissue samples." *BioTechniques* 15(3): 532-534, 536-537.
Erdman, D. D. and L. J. Anderson (1990). "Monoclonal antibody-based capture enzyme immunoassays for specific serum immunoglobulin G (IgG), IgA, and IgM antibodies to respiratory syncytial virus." *J Clin Microbiol* 28(12): 2744-2749.
Li, D., D. A. Jans, et al. (2008). "Association of respiratory syncytial virus M protein with viral nucleocapsids is mediated by the M2-1 protein." *J Virol* 82(17): 8863-8870.
Murray, J., C. Loney, et al. (2001). "Characterization of monoclonal antibodies raised against recombinant respiratory syncytial virus nucleocapsid (N) protein: identification of a region in the carboxy terminus of N involved in the interaction with P protein." *Virology* 289(2): 252-261.
Reichert, J. M. "Antibody-based therapeutics to watch in 2011." *MAbs* 3(1).
van den Hoogen, B. G., S. Herfst, et al. (2004). "Antigenic and genetic variability of human metapneumoviruses." *Emerg Infect Dis* 10(4): 658-666.

The invention claimed is:

1. Monoclonal antibody or a fragment thereof that binds to the M2-1 protein of human respiratory syncytial virus (RSV), comprising a heavy chain variable region according to SEQ ID NO:3 (IgGV$_H$-8A4/G9) and a light chain variable region according to SEQ ID NO:4 (IgκV$_L$-8A4/G9).

2. A set of nucleotide sequences which encode a monoclonal antibody or a fragment thereof that binds to the M2-1 protein of human respiratory syncytial virus (RSV) according to claim 1, wherein the set comprises SEQ ID NO:1 encoding the heavy chain variable region of the antibody and/or SEQ ID NO:2 encoding the light chain variable region of the antibody.

3. A diagnostic method for RSV infection in a biological sample, the method comprising contacting the biological sample with the monoclonal antibody against RSV or a fragment thereof according to claim 1 such that the monoclonal antibody against RSV or fragment thereof binds to the M2-1 protein of RSV present in the sample; and detecting antibody-antigen binding.

4. The diagnostic method according to claim 3, wherein the biological sample is selected from the group consisting of in vitro cells infected with RSV, nasal secretions, nasal washes, pharyngeal secretions and/or washings or bronchial secretions.

5. The diagnostic method according to claim 3, wherein the detecting step comprises a technique selected from ELISA, immunofluorescence, immunohistochemistry, immunochromatography, flow cytometry, cellsorter, immunoprecipitation, and Western blot.

6. The diagnostic method according to claim 3, wherein the antibody or fragment thereof is conjugated with a label which allows its detection.

7. The diagnostic method according to claim 3, wherein the antibody is bound to a label selected from the group consisting of fluorophores, biotin, radioisotopes, enzymes and metals.

8. A diagnostic kit for detecting RSV, comprising the monoclonal antibody against RSV according to claim 1.

9. The diagnostic kit according to claim 8, wherein the antibody is attached to a solid support.

10. The diagnostic kit according to claim 9, wherein the solid support is a membrane formed by one of the compounds selected from the group consisting of nitrocellulose, cellulose, polyethylene and nylon.

11. The diagnostic kit according to claim 10, wherein the kit corresponds to an immunochromatographic test.

* * * * *